United States Patent [19]

Dorsett

[11] Patent Number: 4,695,537

[45] Date of Patent: Sep. 22, 1987

[54] PARTICLES SENSITIZED WITH DETERGENT-TREATED ANTIGEN FOR AGGLUTINATION IMMUNOASSAY

[75] Inventor: Preston H. Dorsett, Memphis, Tenn.

[73] Assignee: The University of Tennessee Research Corp., Knoxville, Tenn.

[21] Appl. No.: 727,661

[22] Filed: Apr. 25, 1985

Related U.S. Application Data

[63] Continuation-in-part of Ser. No. 380,537, May 21, 1982, Pat. No. 4,590,156.

[51] Int. Cl.[4] ................. G01N 33/546; G01N 33/547
[52] U.S. Cl. .......................................... 435/5; 435/7; 435/810; 436/510; 436/532; 436/533; 436/534; 436/808

[58] Field of Search ............... 436/533, 534, 825, 510, 436/532, 808; 435/5, 7, 810

[56] References Cited

U.S. PATENT DOCUMENTS

| | | | |
|---|---|---|---|
| 4,060,597 | 11/1977 | Sato | 436/534 |
| 4,292,038 | 9/1981 | Kondo | 436/825 X |
| 4,311,788 | 1/1982 | Heuck | 436/825 X |
| 4,362,531 | 12/1982 | de Steenwinkel | 436/825 X |
| 4,536,478 | 8/1985 | Sokoloff | 436/825 X |
| 4,600,698 | 7/1986 | Toth | 436/825 X |

*Primary Examiner*—Sidney Marantz
*Attorney, Agent, or Firm*—Elliot M. Olstein

[57] ABSTRACT

An agglutination immunoassay for antibody wherein antigen for sensitizing a solid particulate support is treated with detergent. The resultant antigen-sensitized support is resistant to self-agglutination.

28 Claims, No Drawings

PARTICLES SENSITIZED WITH DETERGENT-TREATED ANTIGEN FOR AGGLUTINATION IMMUNOASSAY

This application is a continuation-in-part of U.S. Application Ser. No. 380,537, filed on May 21, 1982 U.S. Pat. No. 4,590,156.

This invention relates to antigens, and more particularly to the use of antigens for the production of sensitized solids, and the use of antigen sensitized solids for testing for antibodies. Most particularly, the invention relates to viral antigens supported on a particulate support and the use thereof in an assay.

U.S. Pat. No. 4,195,074 discloses a process for producing soluble rubella virus antigen, and the use thereof in an agglutination test for rubella virus antibody. In accordance with U.S. Pat. No. 4,195,074, the cell culture fluid from rubella virus-infected cells is subjected to immunosorbent separation through a column containing IgG derived from human serum known to contain antibodies reactive with rubella virus antigen followed by elution of the rubella virus antigen material from the column and selection of the soluble antigen by gel permeation chromatography. The antigen may then be employed for sensitizing erythrocytes, and the sensitized erythrocytes are used to determine antibody in human serum samples by direct agglutination.

In accordance with one aspect of the present invention, there is provided a solid support sensitized with an antigen with the antigen preferably being derived from an intracellular parasite, in particular, a virus.

More particularly, the antigen, which is supported on the solid particle(s) (a particulate support) has been treated with a detergent or surfactant so as to produce a particulate support sensitized with antigen which is more resistant to self-agglutination. Although applicant does not intend to be bound by any reasoning, it is believed that treating the antigen with the surfactant disrupts the antigen on the solid particles and such disrupted antigen on solid particles results in an increase in the resistance to self-agglutination. It is believed that the treatment disrupts the antigen and that such disruption may reduce the molecular weight which improves resistance to self-agglutination.

In accordance with a preferred embodiment, the antigen is treated with the detergent prior to being supported on the solid support; however, it is also possible to treat the antigen after being supported. Treatment on the support generally results in a loss in titer and, therefore, is not preferred.

The antigens which are treated prior to being supported on the particulate support are antigens which have a high molecular weight in excess of 500,000 daltons and in particular, antigens from an intra-cellular parasite such as a virus, toxoplasma, chlamydia or mycoplasma.

The treatment of the antigen with the detergent prior to being supported on the particulate support, may occur simultaneously with recovery of the antigen and prior to being supported on the solid particle(s).

Thus, for example, a viral antigen may be recovered from intact virus by treating the virus with a detergent (surfactant) which disrupts the virus to provide the viral antigen and in such a case, the viral antigen may be supported on a solid particle to produce a sensitized particle which resists self-agglutination in that the viral antigen is treated with the detergent or surfactant prior to being supported on the solid support.

In the case where the antigen is recovered by a procedure which does not involve the use of a detergent or surfactant, then the recovered antigen is separately treated to disrupt the antigen prior to supporting the antigen on the solid particles so as to provide sensitized particles which resist self-agglutination.

The surfactant or detergent which is used for treating the antigen may be any one of a wide variety of surfactants or detergents which disrupt the antigen, without destroying the antigenic characteristics, including cationic, anionic and non-ionic surfactants. Such surfactants are well known in the art, and as representative examples, there may be mentioned alkali metal salts of sulfates, soaps, sulfated or sulfonated oils, various amines, quaternary salts, condensation products with ethylene oxide, etc. Preferred detergents for such use are alkali (lithium or sodium) dodecyl sulfate, sulfobetain, deoxylcholate and laurolylsarcosine (Sarcosyl).

As hereinabove indicated, it is believed that the antigen is disrupted so as to reduce its molecular weight and the detergent is preferably employed in an amount and for a time such as to effect such molecular weight reduction. In accordance with a preferred embodiment, the molecular weight of the antigen does not exceed 200,000 daltons and most generally does not exceed 150,000 daltons, as determined by sucrose gradient centrifugation or exclusion chromatography.

In general, the surfactant or detergent is employed in a weight ratio of surfactant to antigen of from about 0.05 to 1 to about 5 to 1. The selection of an optimum amount is deemed to be within the scope of those skilled in the art from the teachings herein.

After treating the antigen with the surfactant or detergent, the antigen may be supported on a solid particulate support. The support may be any one of a wide variety of supports, and as representative examples of suitable supports there may be mentioned synthetic polymer supports, such as polystyrene, polypropylene, substituted polystyrene (e.g., aminated or carboxylated polystyrene), polyacrylamides, polyamides, polyvinylchloride, etc.; glass beads, agarose; cellulose; etc. The supports may be provided with reactive groups; e.g., carboxyl groups, amino groups, etc. to permit direct linking of the virus antigen to the support.

The antigen may be supported on the support by a variety of techniques including adsorption; covalent coupling; for example, by activation of the support, or by the use of a suitable coupling agent or by the use of reactive groups on the support. Such procedures are generally known in the art, and no further details are deemed necessary for a complete understanding of the present invention.

In accordance with a particularly preferred embodiment, the antigen is supported on a particulate support by an adsorption technique, although other techniques may be used.

In accordance with preferred embodiment, the particulate support is either a polystyrene, aminated polystyrene, carboxylated polystyrene or a polyvinylchloride, although, it is to be understood that the scope of the invention is not limited to such supports.

As hereinabove indicated, the antigen may be supported on the support by the use of an adsorption technique, or by covalent coupling with a coupling agent. As representative examples of suitable coupling agents there may be mentioned: dialdehydes; for example, glutaraldehyde, succinaldehyde, malonaldehyde, etc.;

unsaturated aldehyde, e.g., acrolein, methacrolein, crotonaldehyde, etc.; carbodiimides; diisocyanates; dimethyladipimate; cyanuric chloride, etc. The selection of a suitable coupling agent should be apparent to those skilled in the art from the teachings herein.

Similarly, the antigen may be supported by activation of a suitable support; for example, cyanogen bromide activated agarose.

The antigen which is treated and supported on a particulate support in accordance with the present invention is preferably a viral antigen. The viral antigen may be recovered in accordance with a variety of procedures.

In accordance with one procedure, which is particularly applicable to recovering a soluble rubella virus antigen, a whole virus is treated with a surfactant or detergent which disrupts the virus to provide the virus antigen, in particular, rubella virus antigen, without destroying the antigenic characteristics thereof. The surfactant or detergent is of the type hereinabove described. In such a procedure, it is not necessary to employ a separate step for treating the viral antigen in addition to the step for recovering the viral antigen by use of the detergent or surfactant.

The surfactant is employed in an amount which is sufficient to disrupt and solubilize the virus and which does not destroy the antigenic characteristics thereof (too much detergent may destroy the antigenic characteristics). In general, the surfactant to virus weight ratio is an amount of from 0.2:1 to about 5:1, preferably from about 0.5:1 to 1:1. The selection of an optimum amount is deemed to be within the scope of those skilled in the art from the teachings herein.

The treatment of the purified virus is effected at a temperature which does not denature the virus proteins, with such temperature generally not exceeding about 30° C., with a temperature of from 20° C. to 25° C. being most convenient. Similarly, the pH is selected so as to maintain stability, with the pH being generally at 8.5, with the optimum pH generally being in the order of from 8.0 to about 9.0.

The treatment of the purified virus with the surfactant is for a period of time sufficient to disrupt the virus and effect solubilization thereof. In general, such disruption and solubilization can be accomplished in time periods in the order of from 5 to 120 minutes, however, in some cases longer or shorter times may be applicable.

The selection of an optimum treatment time is deemed to be within the scope of those skilled in the art from the teachings herein.

Applicant has found that by using a surfactant to disrupt and solubilize the whole rubella virus, as hereinabove described, it is possible to provide soluble rubella virus antigen which retains its antigenicity.

A procedure for disruption and solubilization of whole virus, as hereinabove described, has been previously practiced in the art; for example, Vaheri et al. "Structural Proteins and Subunits of Rubella Virus", *Journal of Virology*, P. 10–16 (Jan. 1972). In addition, it is known that such a procedure is capable of recovering the structural proteins of the whole rubella virus, with there being three principal structural proteins, namely a structural protein with a molecular weight in the order of from 60,000 to 65,000 daltons, a structural protein with a molecular weight in the order of from 40,000 to 50,000 daltons, and a structural protein having a molecular weight in the order of from 32,000 to 38,000 daltons. Applicant has also found evidence of structural proteins having molecular weights of from 100,000 to 120,000 daltons.

Applicant has found that the structural proteins recovered by such a procedure retain antigenic characteristics, and in addition, such structural proteins can be used in an assay for rubella antibody. Furthermore, applicant has found that such structural proteins are capable of detecting early phase rubella antibody, i.e., the rubella antibody present in serum or plasma within ten days of onset of rubella rash. The term "rubella virus antigen" as used herein encompasses one or more of such structural proteins recovered by such procedure.

The hereinabove described technique for disruption and solubilization of whole rubella virus to provide soluble rubella virus antigen is also applicable to providing virus antigen from other viruses; e.g., those hereinafter disclosed with reference to a purification of virus. Such viral antigens may then be supported on a solid support to provide a solid sensitized with the viral antigen for use in an assay.

In accordance with an aspect of the present invention, applicant has found that disruption and solubilization of whole rubella virus produces a soluble product which is antigenic and which is capable of reacting with rubella antibody, including the early phase antibody. Thus, by using a product prepared by such a procedure in an assay for rubella antibody; and in particular, on a solid support, it is possible to detect rubella antibody even during the early phase.

The recovered product is of particular value for a direct agglutination assay, and applicant has found that such soluble rubella virus antigen may be supported on a latex particle (in particular, a polystyrene) without the problem of self-agglutination.

The purified whole virus which is treated with surfactants is a virus which is produced in a tissue culture by procedures known in the art, and which is subsequently purified to remove non-virus lipids, nucleic acids, and non-viral proteins.

The tissue culture growth of rubella virus wherein rubella virus infected cells are raised in a suitable culture medium is well known in the art. The cells that are suitable for tissue culture growth to propagate the rubella virus include Vero cells, Baby Hamster Kidney, Procine Stabile Kidney; Serum Institute Rabbit Cornea and the like. In general, tissue cultures conventionally used for producing rubella virus are also suitable for the purposes of the present invention.

The virus may then be purified by procedures known in the art; e.g., as disclosed by Vaheri, et al., supra. In accordance with a preferred embodiment, the virus is purified in accordance with a new procedure.

More particularly, such procedure for purifying virus involves treating concentrated virus with hydroxylapatite gel in an aqueous solution of controlled ionic strength and pH.

More particularly, after filtration and concentration, the virus is contacted with hydroxyl apatite gel in an aqueous solution having an ionic strength which is great enough to minimize or prevent adsorption of the virus by the gel, and which is low enough to allow the non-virus proteins to be adsorbed by the gel. The ionic strength is maintained by use of phosphate ions, with the phosphate ions being present at a molarity of from 0.05M to 1.5M to provide for effective adsorption of non-virus proteins and nucleic acids, without significant adsorption of the virus. The phosphate molarity in most cases is at least 0.08M.

In addition, the adsorption is conducted at a pH in the order of from 6 to 9, most generally in the order of from 7 to 8. The pH of the solution is maintained by the use of a suitable buffer. The adsorption may be conducted in the presence of EDTA at a concentration from 0.01M to 0.001M. EDTA, as well as other chelating agents, increases adsorption of non-viral proteins and nucleic acids, and aids in minimizing the adsorption of viral proteins.

By proceeding in accordance with such purification, the high molecular weight proteins and nucleic acids are adsorbed by the gel to thereby separate the virus protein from the non-viral proteins having similar molecular weights.

After such adsorption, the lower molecular weight proteins still remaining in the fluid may be separated by conventional procedures. Thus, for example, further separation may be accomplished by centrifugation through a barrier layer or cushion as known in the art. In particular, the virus protein is centrifuged through a suitable barrier layer such as sucrose, glycerol, cesium chloride, cesium sulfate and the like, with the lower molecular weight proteins remaining above the barrier, and the virus being centrifuged through the barrier, as a separate layer. The fluid containing the low molecular weight proteins and the barrier layer are then removed leaving a virus protein essentially free of non-virus proteins, nucleic acids, lipids, and the like. In general, the purified virus contains less than 1%, most generally less than 0.1% of non-virus lipids, nucleic acids and proteins Such purified virus may then be treated with a surfactant to disrupt the virus and effect solubilization thereof to thereby provide a virus antigen, as hereinabove described.

It is to be understood that, although the hereinabove described procedure for purifying the rubella virus is preferred, other procedures for separating non-virus proteins, lipids and nucleic acids can also be employed for purifying the rubella virus for subsequent treatment with surfactant to thereby produce the soluble rubella virus.

The antigen and in particular, a viral antigen, may be obtained by other procedures. Thus, for example, as described in U.S. application Ser. No. 700,806, filed on Feb. 11, 1985, antigen may be recovered from cells containing an intra-cellular parasite (in particular, a virus) by extracting the antigen from the cells with an aqueous salt solution.

More particularly, the aqueous salt solution is hypertonic with respect to the osmolarity of the cells and is a salt solution which does not adversely affect the immunoreactivity of the extracted antigen. The aqueous salt solution is one which extracts the antigen from the cell without essential destruction of the cells; i.e., the cells remain essentially intact.

The salt may be either an inorganic or an organic salt which is soluble in water, and as representative examples of such salts, there may be mentioned: potassium chloride, guanidine hydrochloride, magnesium chloride, potassium thiocyanate, sodium chloride, etc. Potassium chloride, magnesium chloride and guanidine hydrochloride are particularly preferred in that the use of such salts results in a higher yield of antigen.

The concentration of salt in the solution is one which provides a hypertonic solution and which effectively extracts the antigen from the cells. In general, the salt concentration is in the order of at least 1.0M and no greater than 5.0M, and preferably at least 2.0M and no greater than 3.5M.

The extraction is accomplished at temperatures which will not denature the antigen. The temperature generally does not exceed about 30° C. The pH of the salt solution is generally maintained at a value so as to maintain stability, with the pH generally being from pH 6 to pH 10. A suitable buffer may be used to maintain the pH.

The cells may be contacted with the salt solution by any one of a wide variety of procedures. Such contacting may be readily accomplished by placing the infected cells in the salt solution and stirring; e.g., with a magnetic stirrer.

After the cells have been contacted for a period of time sufficient to extract the antigen from the cells, the cells are removed from the salt solution; for example, by centrifugation.

The remaining supernatant contains the antigen, and the antigen may be stored for use at a subsequent time, or may be used as hereinafter described.

The salt may be removed from the supernatant, for example, by dialysis of the supernatant against a suitable buffer.

The above procedure is particularly applicable to extracting viral antigen from cells infected with a virus and most particularly to recovering CMV antigen from CMV infected cells. The cells which are infected with CMV are preferably primary human foreskin cells; however, it is to be understood that other cells may be used within the spirit and scope of the invention; for example, human diploid cells other than foreskin cells.

The viral antigens recovered by this procedure and in particular, CMV antigen, after treatment with detergent, may be supported on a solid particulate support for use in an assay.

An antigen sensitized particulate support prepared in accordance with the invention is preferably prepared for use in an assay in which antibody is determined by an agglutination technique. The particulate support is provided with an effective amount of the antigen for the assay, while preventing excessive amounts which may result in bridging of the antibody to a single particle. In general, the weight ratio of antigen to support is from 1:100 to 1:5000. The selection of an optimum amount is deemed to be within the scope of those skilled in the art from the teachings herein.

In accordance with one technique, after the antigen is adsorbed on the particles, the support, including the adsorbed antigen, is further coated with protein which does not adversely affect the subsequent immunochemical reaction in order to provide a protein coating on the portion of the support which does not include the antigen. As should be apparent, the protein coating should not immunologically react with either the antigen or with sera to be used in the assay. As examples of suitable proteins there may be mentioned: bovine serum albumin, ovalbumin, and the like. The selection of a suitable protein to saturate the spaces between the antigen on the support is deemed to be within the scope of those skilled in the art from the teachings herein.

It is to be understood that such coating with protein is not required for producing sensitized particles for use in an agglutination assay.

After the antigen has been supported on a solid support, as generally practiced in the art for the production of sensitized particles for use in an agglutination assay, the sensitized particles are treated with a liquid containing polyoxyethylene sorbitan monolaurate (Tween 20) at a weight ratio to the polystyrene of 0.05:1 to 10:1.

The sensitized particles are preferably a synthetic polymer and in particular, a polystyrene [substituted (carboxylated or aminated) or unsubstituted] or polyvinylchloride latex. Applicant has found that sensitization of such particles with antigen prepared, as hereinabove described, produces a sensitized particle which is more resistant to self-agglutination, whereby such sensitized latex particles may be effectively employed in a direct agglutination assay for antibody. In the case where the antigen is rubella virus antigen, such sensitized particles are capable of detecting early phase rubella antibody. In addition, such sensitized particles are capable of providing a direct agglutination assay having a high sensitivity for rubella antibody.

The antigen sensitized particles prepared in accordance with the invention are suitable for use in a kit and assay for antibody by a direct agglutination procedure. Such kit may include, in addition to the sensitized particles, as hereinabove described, in a suitable container therefor, a reactive serum control (contains antibody) and a non-reactive serum control (no antibody) in suitable containers therefor. In accordance with a preferred embodiment, in addition to the reagents, there is provided a test card on which the assay is effected. The test card has a flat testing surface which includes suitably marked areas (for example, a test circle) for placing one or more samples to be assayed, as well as suitably marked areas for each of the serum controls. The test card and reagents may be included in a single kit package.

In the agglutination assay, undiluted serum or diluted serum (e.g., 1:10) is contacted with the sensitized particles followed by mixing, with the presence of the antibody against the antigen (in particular, a viral antigen) being evidenced by visible agglutination.

Such antigen sensitized particles may also be employed in a quantitative assay for antibody; in particular, rubella virus antibody and CMV antibody.

In a quantititative assay, the sample to be assayed is serially diluted, as appropriate, and to each serial dilution there is added the particles sensitized with the antigen. The quantity of antibody in the sample is determined from the highest dilution giving any agglutination of the sensitized particles.

The quantitative or qualitative assay for antibody may be effected on a card surface wherein the surface includes suitably marked areas for placing the sample and control to which the sensitized particles are added.

The invention has particular applicability to sensitizing particles for use in determining rubella virus or cytomegalo virus (CMV); however, the scope of the invention is not limited to such viruses.

The invention will be further described with respect to the following examples: however, the scope of the invention is not to be limited thereby:

EXAMPLE I

Production and Purification of Rubella Virus.

Confluent roller cultures (680 cm$^2$) of Vero cells (a continuous culture line of cells derived from African Green monkey kidney) were innoculated with approximately 0.01 PFU of rubella virus per cell and maintained in a standard culture medium (Medium 199) containing 0.025 herpes buffer, pH 7.4, and 2% (vol/vol) of the filtrate obtained by forcing fetal bovine serum through a xembrane designed to retain molecules of 100,000 molecular weight and greater (Amicon XM-100 membrane). The medium was changed daily, and the culture fluids having a hemagglutination titer greater than 16 were made to contain 0.01M Tris base and 0.01M EDTA. After incubation at 4° C. for 1 hour, they were concentrated in an Amicon hollow fiber dialyzer-concentrator to 1/10 the original volume. After clarification at 5,000×g for 20 minutes, the pH was adjusted to 7.6 at 22° C. and 1/10 volume of hydroxylapatite suspension was added, and the slurry was incubated at 4° C. with mixing, overnight. The hydroxylapatite was removed by centrifugation at 5,000×g for 15 minutes, after which 30 ml of the concentrate was layered over 9 ml of 69% (wt/wt) glycerol in a Beckman SW28 tube The virus was sedimented at 82,000×g for 16 hours at 4° C., and the resultant pellet was resuspended in 0.01M carbonate buffer, pH 9.5 (coating buffer) The purified virus was assayed for hemagglutinin content and stored at -70° C.

EXAMPLE II

Solubilization of Purified Virus.

The purified virus in 0.01M carbonate buffer, pH 9.5, was solubilized by treatment with sodium dodecyl sulfate (SDS). The purified virus was made to contain 0.05% (w/v) SDS and was incubated for 30 minutes at room temperature.

EXAMPLE III

Preparation of Sensitized Latex.

Commercial suspensions of polystyrene latex (0.9 micron diameter particles) were washed four times with 25 volumes each of the coating buffer and were resuspended in the coating buffer to provide 3% solids (vol/vol.). The latex suspension was added directly to the solubilized virus at a ratio of 2 volumes of the 3% latex to 1 volume of solubilized virus and the suspension was mixed by tumbling for 16 hours at room temperature. The sensitized latex was washed twice with 20 volumes of 1% bovine serum albumin in phosphate buffered saline (BSA-PBS) and resuspended at 0.5% in 1% BSA-PBS contained 0.05% polyoxyethylene sorbitan monolaurate surface active agent (Tween 20) and 0.02% gentamiacin.

EXAMPLE IV

Latex Agglutination Test for Rubella Virus Antibodies.

Glass plates with 1.4 cm fused circles were employed. Serial 2-fold dilutions of serum were prepared in 1% BSA-PBSTween 20 and 25 ul of each dilution was placed in separate wells. After adding 25 ul of sensitized latex, the serum and latex suspension was mixed and rotated 100 rpm for 5 minutes. The presence of antibody against rubella virus was evidenced by visible agglutination.

EXAMPLE V

Purified virus prepared in accordance with Example I was treated with a 1% aqueous solution of sarcosyl for 30 minutes at room temperature in coating buffer to disrupt and solubilize the virus.

The pH of the solubilized virus was adjusted to 6.5 with hydrochloric acid and mixed with two volumes of 3% carboxylated polystyrene latex (in phosphate buffer, pH 6.5) for 1 hour at 4° C.

To the solution was added 10 mg of a carbodiimide coupling agent and the mixture was mixed overnight at 4° C.

After centrifugation, the solids were resuspended in phosphate buffered saline (PBS) followed by centrifugation and resuspension in PBS containing 1% BSA and 0.05% Tween 20.

The procedure covalently bound the soluble rubella virus antigen to the latex.

EXAMPLE VI

In accordance with a preferred procedure, there is provided a test card for rubella antibody. The test card includes a marked circle for a reactive control, a marked circle for non-reactive control, as well as one or more test sample circles.

25 ul of undiluted serum sample is placed in appropriately marked sample circle, and 25 ul of the reactive and non-reactive controls are placed in their respective circles.

With a micropipettor, there is added sensitized latex of Example III (approximately 15 ul), followed by rotation on a rotator (about 8 minutes), and gentle hand rotation.

The card is read microscopically in the wet state under a high intensity incandescent lamp.

The reactive control should show definite agglutination and the non-reactive control should show no agglutination.

Any serum samples showing any agglutination should be reported as reactive.

EXAMPLE VII

Primary human foreskin cells are infected with AD 169 CMV and incubated for 7 to 10 days at 37° C., followed by harvesting of the infected cells. The cells are scraped into phosphate buffered saline (PBS), and the cells are collected by centrifugation followed by resuspending of the cells in 3M KCL in 0.1M glycine, NaOH .pH 7.5. The mixture is maintained at 4° C. for 24 hours, with gentle mixing, to extract CMV antigen from the infected cells. After such period, the cells are removed by centrifugation and the supernatant is dialyzed against 1000 volumes of 0.1M Glycine. NaOH pH 7.5. The CMV antigen may be stored by freezing at -70° C.

After determining the protein content from the optical density at 260 mm and 280 mm, the CMV antigen is treated with SDS (0.25 mg. SDS per mg. of CMB antigen).

Commercial suspensions of polystyrene latex (0.9 micron diameter particles) are washed with carbonate buffer and then resuspended in the carbonate buffer to provide 3% solids (volume to volume).

The hereinabove treated CMV antigen is added to the 3% latex suspension and incubated at 4° C. overnight with tumbling.

The latex is washed with phosphate buffered saline and then resuspended in a phosphate buffered saline solution to which has been added 1% ($^w$/v) bovine serum albumin and 0.1% ($^v$/v) polyoxyethylene sorbitan monolaurate surface active agent (Tween 20) and 0.02% gentamicin. The sensitized latex is allowed to cure for 24 hours at 4° C. with gentle stirring.

The sensitized latex may be employed in a test for CMV antibody by use of a test card which includes a marked circle for a reactive control, a marked circle for a non-reactive control, as well as one or more test samples circles.

25 ul of undiluted serum sample is placed in an appropriate marked serum sample circle, and 25 ul of the reactive and unreactive controls are placed in their respective circles.

With a micropipettor, there is added the sensitized latex (approximately 15 ul), prepared as hereinabove described, followed by rotation on a rotator, and gentle hand rotation.

The card is read microscopically in the wet state under a high intensity incandescent lamp while rotating gently by hand.

The reactive control should show definite agglutination and the non-reactive should show no agglutination.

Any serum sample showing any agglutination should be reported as reactive.

Although the invention has been previously described with respect to CMV and rubella antigen, and an assay employing supported CMV and rubella antigen for determining CMV and rubella antibody, it is to be understood that the teachings are also applicable to other viral antigens, including but not limited to: other herpes viruses, such as varicella Zoster, Epstein-Barr (infectious Mono-Nucleosis); measles virus (rubeola); para-influenza viruses; influenza virus; dengue virus, etc.

Similarly, the invention is applicable to supporting on a particulate support antigens from intra-cellular parasites other than viruses, such as toxoplasma, chlamydia, microplasma, etc.

The above modifications and others should be apparent to those skilled in the art from the teachings herein.

The present invention is advantageous in that it is possible to support an antigen, in particular, CMV or rubella antigen, on a particulate support wherein the antigen sensitized particles are resistant to self-agglutination; in particular, where the antigen is supported on latex particles for use in an agglutination type of assay. These and other advantages should be apparent to those skilled in the art from the teachings herein.

Numerous modifications and variations of the present invention are possible in light of the above teachings and, therefore, within the scope of the appended claims, the invention may be practiced otherwise than as particularly described.

What is claimed is:

1. A composition, comprising:
   a solid particulate support and a detergent-treated antigen supported on said support, said antigen being an intracellular parasite antigen, said antigen having been treated with a detergent to provide a solid support sensitized with the detergent-treated antigen which is resistant to self-agglutination.

2. In a kit for determining antibody by an agglutination technique, the improvement comprising.
   said kit including in a reagent container the solid particulate sensitized with the detergent-treated antigen of claim 1.

3. The kit of claim 2 wherein said kit further includes a test card having a flat surface for receiving assay samples.

4. The kit of claim 3 wherein the solid particulate support is polystyrene latex.

5. The kit of claim 3 and further comprising in separate reagent containers a reactive serum control antibody and a non-reactive serum control free of antibody.

6. The composition of claim 1 wherein said antigen has been treated with a detergent prior to being supported on the support.

7. In a direct agglutination assay for an antibody employing solid particles sensitized with antigen, the improvement comprising:

contacting a sample containing a suspected antibody with, the solid particles sensitized with the detergent-treated antigen of claim 2, said suspected antibody becoming immunobound by said detergent-treated antigen.

8. The assay of claim 7 wherein the antigen is a viral antigen.

9. The assay of claim 7 wherein the antigen is a rubella virus antigen.

10. The composition of claim 6 wherein the solid support is a synthetic polymer.

11. The composition of claim 10 wherein the synthetic polymer is selected from the group consisting of polyvinylchloride, polystyrene, aminated polystyrene and carboxylated polystyrene.

12. The composition of claim 10 wherein the antigen is covalently coupled to the solid support.

13. The composition of claim 10 wherein the antigen is adsorbed on the solid support.

14. The composition of claim 13 wherein the antigen is a herpes virus antigen.

15. The composition of claim 13 wherein the detergent is an alkali dodecyl sulfate.

16. The composition of claim 13 wherein the antigen is a viral antigen.

17. The composition of claim 16 wherein the antigen is rubella virus antigen.

18. The composition of claim 16 wherein the antigen is CMV antigen.

19. A process for producing a solid particulate support sensitized with a detergent-treated antigen, which is resistant to self-agglutination, comprising:

contacting an intracellular parasite antigen with a detergent and supporting the detergent-treated antigen on a solid particulate support.

20. The process of claim 19 wherein the solid support is a synthetic polymer.

21. The process of claim 20 wherein the synthetic polymer is selected from the group consisting of polyvinylchloride, polystyrene, aminated polystyrene and carboxylated polystyrene.

22. The process of claim 20 wherein the antigen is covalently coupled to the solid support.

23. The process of claim 20 wherein the antigen is adsorbed on the solid support.

24. The process of claim 23 wherein the antigen is a herpes virus antigen.

25. The process of claim 23 wherein the detergent is an alkali dodecyl sulfate.

26. The process of claim 23 wherein the antigen is a viral antigen.

27. The process of claim 26 wherein the antigen is rubella virus antigen.

28. The process of claim 26 wherein the antigen is CMV antigen.

* * * * *